(12) United States Patent
Von Oepen et al.

(10) Patent No.: US 6,602,285 B1
(45) Date of Patent: Aug. 5, 2003

(54) COMPACT STENT

(75) Inventors: Randolf Von Oepen, Hirrlingen (DE); Gerd Seibold, Ammerbuch (DE)

(73) Assignee: Jomed GmbH (DE)

( * ) Notice: Subject to any disclaimer, the term of this patent is extended or adjusted under 35 U.S.C. 154(b) by 0 days.

(21) Appl. No.: 09/582,318

(22) PCT Filed: Sep. 2, 1999

(86) PCT No.: PCT/EP99/06456

§ 371 (c)(1),
(2), (4) Date: Jun. 23, 2000

(87) PCT Pub. No.: WO00/13611

PCT Pub. Date: Mar. 16, 2000

(30) Foreign Application Priority Data

Sep. 5, 1998 (DE) .......................... 198 40 645

(51) Int. Cl.⁷ .................................................. A61F 2/06
(52) U.S. Cl. ..................................................... 623/1.17
(58) Field of Search ............................... 623/1.12, 1.15, 623/1.16, 1.17, 1.18, 1.2; 606/198, 194, 195, 191, 192

(56) References Cited

U.S. PATENT DOCUMENTS

| | | |
|---|---|---|
| 5,514,154 A | 5/1996 | Lau et al. |
| 5,569,295 A | 10/1996 | Lam |
| 5,630,829 A | 5/1997 | Lauterjung |
| 5,649,952 A | 7/1997 | Lam |
| 5,695,516 A | 12/1997 | Fischell et al. |
| 5,707,386 A | 1/1998 | Schnepp-Pesch et al. |
| 5,707,388 A | 1/1998 | Lauterjung |
| 5,716,393 A | 2/1998 | Lindenberg et al. |
| 5,728,158 A | 3/1998 | Lau et al. |
| 5,735,893 A | 4/1998 | Lau et al. |
| 5,741,327 A | 4/1998 | Frantzen |
| 5,776,161 A | 7/1998 | Globerman |
| 5,776,183 A | 7/1998 | Kanesaka et al. |
| 5,800,526 A | 9/1998 | Anderson et al. |
| 5,807,404 A | 9/1998 | Richter |
| 5,814,063 A | 9/1998 | Freitag |
| 5,827,321 A | 10/1998 | Roubin et al. |
| 5,836,964 A | 11/1998 | Richter et al. |
| 5,843,120 A | 12/1998 | Israel et al. |
| 5,843,164 A | 12/1998 | Frantzen et al. |
| 5,853,419 A | 12/1998 | Imran |
| 5,860,999 A | 1/1999 | Schnepp-Pesch et al. |
| 5,861,027 A | 1/1999 | Trapp |
| 5,876,449 A | 3/1999 | Starck et al. |
| 5,895,406 A | 4/1999 | Gray et al. |
| 5,922,021 A * | 7/1999 | Jang .......................... 623/1.15 |

(List continued on next page.)

FOREIGN PATENT DOCUMENTS

| | | |
|---|---|---|
| EP | 0 699 451 | 3/1996 |
| EP | 0 808 614 | 11/1997 |
| EP | 0 983 753 | 3/2000 |
| EP | 0 950 386 | 4/2000 |
| EP | 1 042 997 | 10/2000 |
| GB | 2 344 053 | 5/2000 |
| JP | 2000312721 | 11/2000 |
| WO | WO 97/12563 | 4/1997 |

*Primary Examiner*—A. Vanatta
(74) *Attorney, Agent, or Firm*—Luce, Forward, Hamilton & Scripps

(57) ABSTRACT

The present invention relates to a stent (1) comprising a tubular flexible body (2) whose wall (3) has a web structure (4) which can pass from a non-expanded state into an expanded state. The web structure (4) comprises a plurality of neighboring web patterns (5, 6) which, in turn, consist of adjoining webs (9, 10 and 9', 10', respectively). The web patterns (5, 6) are interconnected. Each web (9, 10 and 9', 10' respectively) comprises three portions (9a, 9b, 9c and 10a, 10b, 10c, respectively) that are arranged at an angle ($\alpha$, $\beta$) relative to one another.

18 Claims, 5 Drawing Sheets

U.S. PATENT DOCUMENTS

| | | |
|---|---|---|
| 5,928,248 A | 7/1999 | Acker |
| 6,123,721 A * | 9/2000 | Jang .......................... 623/1.15 |
| 6,179,868 B1 * | 1/2001 | Burpee et al. ............. 623/1.17 |
| 6,190,403 B1 * | 2/2001 | Fischell et al. ............ 623/1.16 |
| 6,193,744 B1 * | 2/2001 | Ehr et al. ................... 623/1.15 |
| 6,193,747 B1 * | 2/2001 | von Oepen ................ 623/1.15 |
| 6,200,334 B1 * | 3/2001 | Jang .......................... 606/198 |
| 6,241,762 B1 * | 6/2001 | Shanley ..................... 623/1.17 |
| 6,258,116 B1 * | 7/2001 | Hojeibane .................. 623/1.16 |
| 6,264,688 B1 * | 7/2001 | Herklotz et al. ........... 623/1.16 |
| 6,299,635 B1 * | 10/2001 | Frantzen .................... 623/1.17 |
| 6,395,020 B1 * | 5/2002 | Ley et al. ................... 623/1.15 |
| 2001/0049549 A1 | 12/2001 | Boylan et al. |

* cited by examiner

COMPACT STENT

FIELD OF THE INVENTION

The present invention relates to a stent according to the preamble of claim 1.

BACKGROUND OF THE INVENTION

Different designs of stents are known from the prior art. These form a vascular prosthesis which consists of a body-tolerated material. Stents are normally used for expanding hollow vessels, such as blood vessels or also body orifices, and for keeping the same in an expanded state. To this end the stent is normally placed in a non-expanded state into a narrow hollow vessel of a patient's body and is subsequently expanded by suitable means, such as a balloon catheter. Normally, the stent body has a web structure comprising several neighboring web patterns which have adjoining webs and are interconnected by means of connection elements.

A fundamental problem encountered in many stent constructions is that these will shorten upon expansion. Such a shortening, however, is undesired because it cannot be ruled out that the expanded stent due to its shortening no longer covers the entire area inside the vessel or orifice, which area is e.g. to be expanded and supported by the stent.

It is therefore the object of the present invention to provide a stent of the type as outlined in the preamble of claim 1, which stent is flexible in the non-expanded state, builds up sufficient holding forces in the expanded state to remain in said state and reduces its length as little as possible during expansion.

SUMMARY OF THE INVENTION

This object is achieved by the features of claim 1.

Since each of the webs of the web patterns comprises three portions that are arranged at an angle relative to one another, this has the effect that upon expansion the angles between the portions will increase, which will minimize or even almost eliminate shrinkage of the stent during expansion.

With such a construction the stent according to the invention is very flexible, preferably in the non-expanded state, such flexibility having a very advantageous effect on the guidability of the stent inside the vessel up to the implantation place, e.g. in the crimped condition on a catheter. Furthermore, the construction according to the invention provides a very stable construction in the expanded state so that the implanted stent can receive great forces, thereby performing an excellent supporting function in the implanted state.

The subclaims relate to advantageous developments of the invention.

Preferably, the portions of each web are made straight.

Furthermore, the webs are subdivided into a central portion and two lateral portions that adjoin the ends of the central portion. The lateral portions preferably enclose obtuse angles with the central portion.

The three portions are preferably arranged relative to one another such that a bowl or plate-like configuration is obtained. Such a configuration, in turn, provides a very compact form during crimping of the stent, as the webs are placed into one another in the manner of plates stacked into one another.

The web patterns are preferably interconnected by connection elements formed as straight webs.

In a particularly preferred embodiment the straight webs extend in a straight line into connection sections of the web patterns which interconnect respectively neighboring webs.

The orientation of the connection elements between two neighboring web patterns is the same. This means that connection elements which are positioned one upon the other have the same orientation. On the other hand, the orientations of the connection elements alternate between two neighboring web patterns so that e.g. when viewing a wall of a stent unwound into the plane one obtains an alternating orientation of the connection elements, once upwards and once downwards.

The stent of the invention has the special advantage that depending on the material used it can be designed either as a self-expanding stent or as a stent which can be expanded by means of a balloon catheter. In both cases its advantageous, previously described characteristics are maintained. If a self-expanding stent is desired, a nickel-titanium alloy should preferably be used as the material.

BRIEF DESCRIPTION OF THE DRAWINGS

Further details, features and advantages of the invention will become apparent from the following description of the embodiment with reference to the drawings, in which.

DETAILED DESCRIPTION OF THE INVENTION

Figure 1:
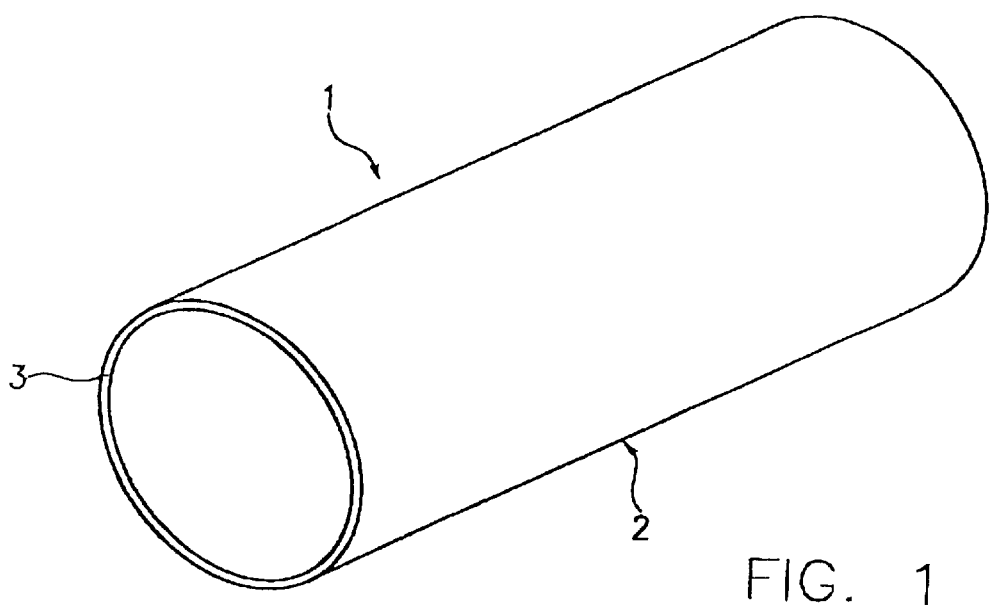
FIG. 1 is a strongly simplified perspective view showing the basic structure of a stent according to the invention.

FIG. 1 is a perspective, schematically simplified view showing a stent 1 comprising a tubular flexible body 2.

The tubular flexible body 2, in turn, comprises a wall 3 having a web structure that will be explained in detail in the following with reference to FIGS. 2 to 4.

Figure 2:
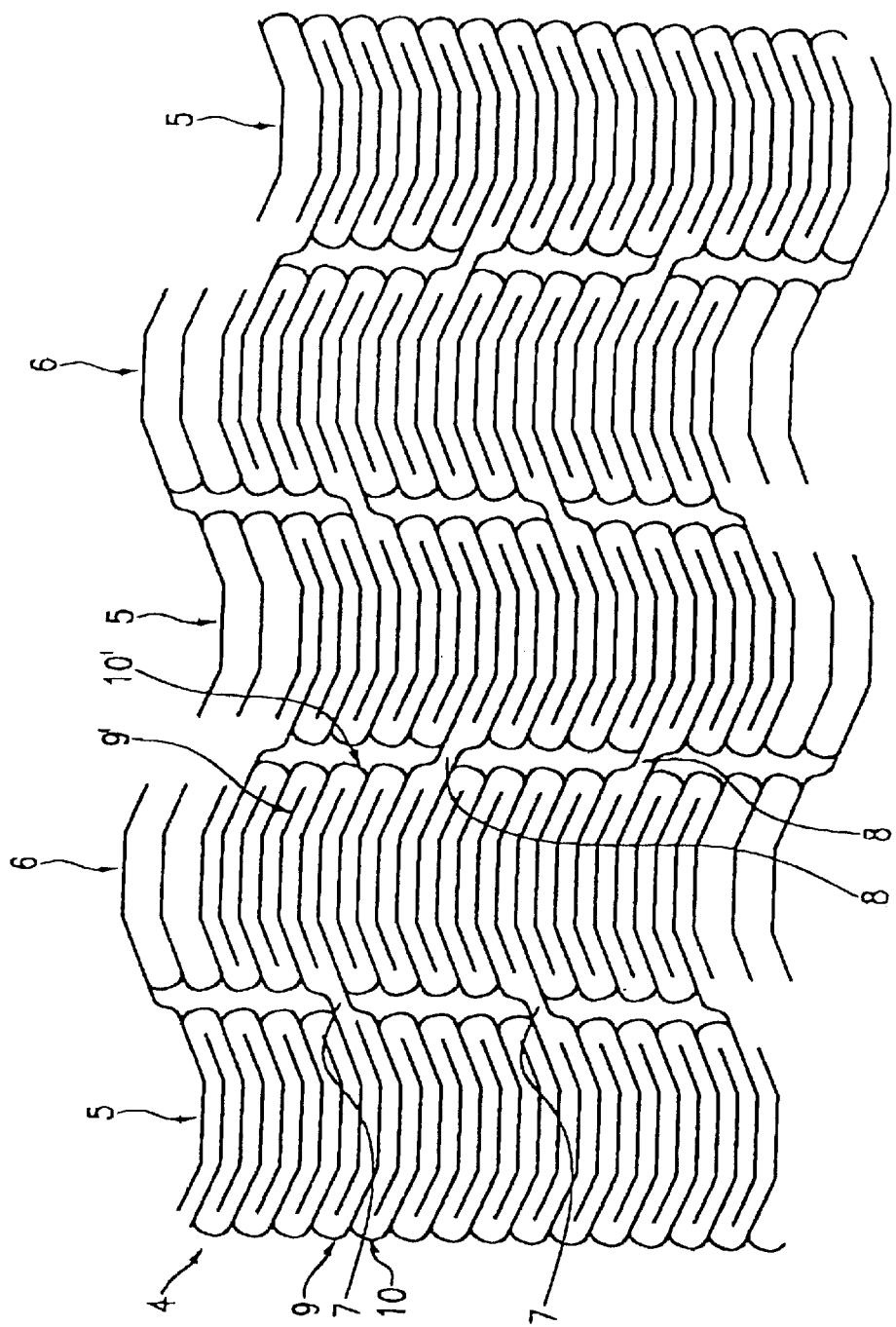
FIG. 2 is a schematically slightly simplified view showing part of the web structure of the wall of the stent according to the invention in the non-expanded state.

FIG. 2 shows the web structure 4 in the non-expanded state.

The web structure 4 comprises neighboring web patterns 5, 6 which are arranged in alternating fashion side by side so that the web patterns according to the section shown in FIG. 2 are arranged in the sequence 5, 6, 5, 6, 5, 6, etc. FIG. 2 illustrates that the web patterns 5 and 6 have adjoining webs 9 and 10. The design of said webs 9, 10 will be described in more detail in the following text; FIG. 2, however, illustrates that the webs 9, 10 have a plate- or bowl-like configuration and open upwards according to the illustration chosen in FIG. 2.

The webs 9', 10' of the neighboring web pattern 6 have the same plate-or bowl-like shape, but open downwards according to FIG. 2.

The web patterns 5, 6 are each interconnected by means of connection elements 7 between the web patterns 5 and 6 and by connection elements 8 between the web patterns 6 and 5. FIG. 2 shows that a plurality of connection elements 7 are provided between the web patterns 5 and 6 and a plurality of connection elements 8 between web patterns 6 and 5, but only two respective connection elements are shown in FIG. 2 because of the sectional view. All of the connection elements 7 have the same orientation which according to the illustration chosen in FIG. 2 extends from the left side, bottom, to the right side, top.

The connection element 8 also have the same orientation among each other, but according to the illustration chosen in FIG. 2 (unwinding of the wall in the plane of FIG. 2) extend from the left side, top, to the right side, bottom. Said orientation alternates between two web patterns 5, 6 and 6, 5, respectively, as shown in FIG. 2.

Figure 3:
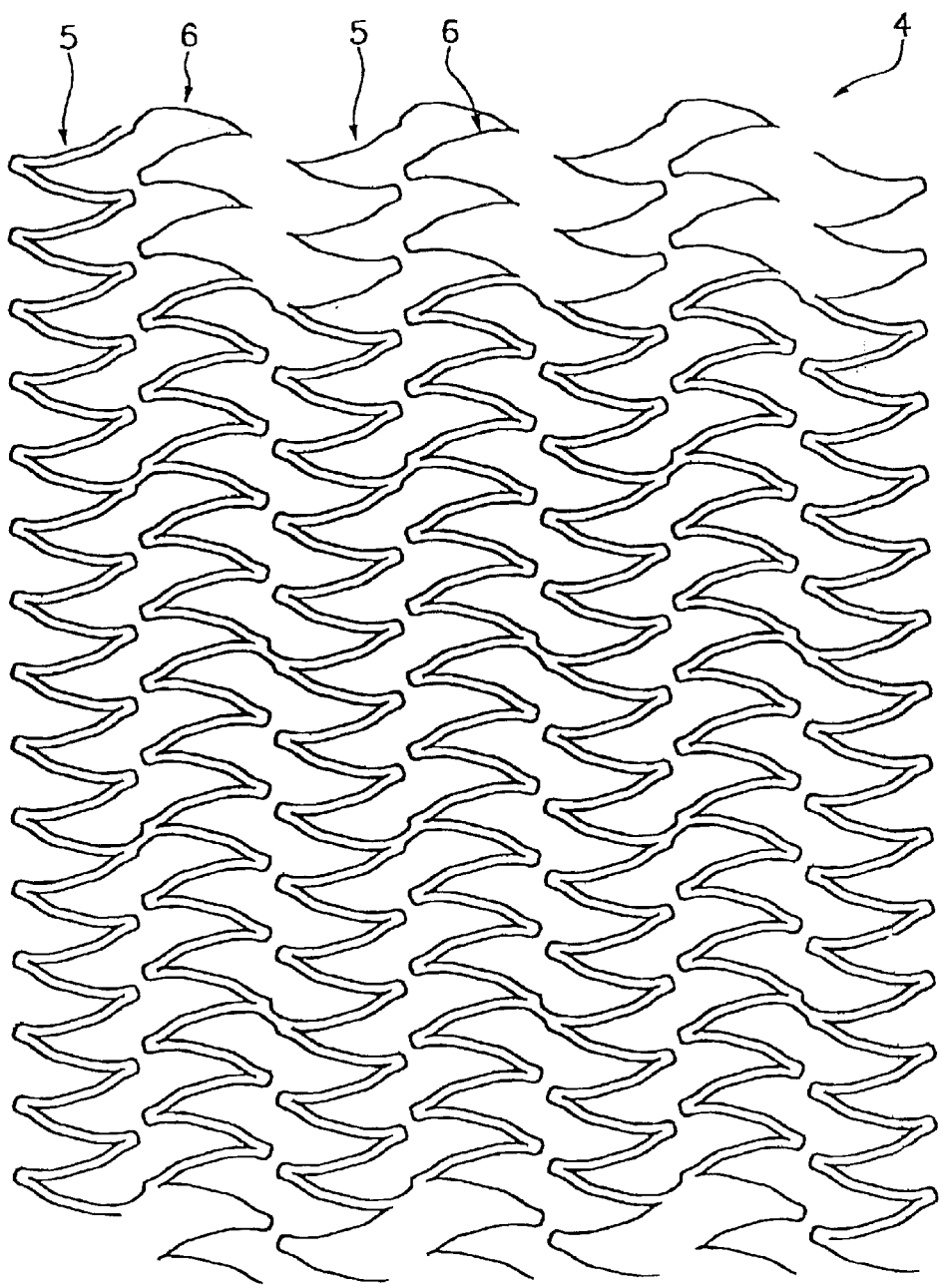
FIG. 3 is a view corresponding to FIG. 2, which shows the web structure of the stent according to the invention in the expanded state.

FIG. 3 illustrates the expanded state of the stent 1, again with reference to a section of the web structure 4 in an illustration where the wall 3 of the body 2 of the stent 1 is unwound into the plane of FIG. 3. FIG. 3 illustrates the spread state of the web structure 4 which gives the stent in the expanded position a high inherent stiffness which enables the stent 1 to remain in said expanded position and permits the reception of radial forces as are e.g. to be received when the stent 1 is implanted into a hollow vessel in the area of a stenosis.

Figure 4:
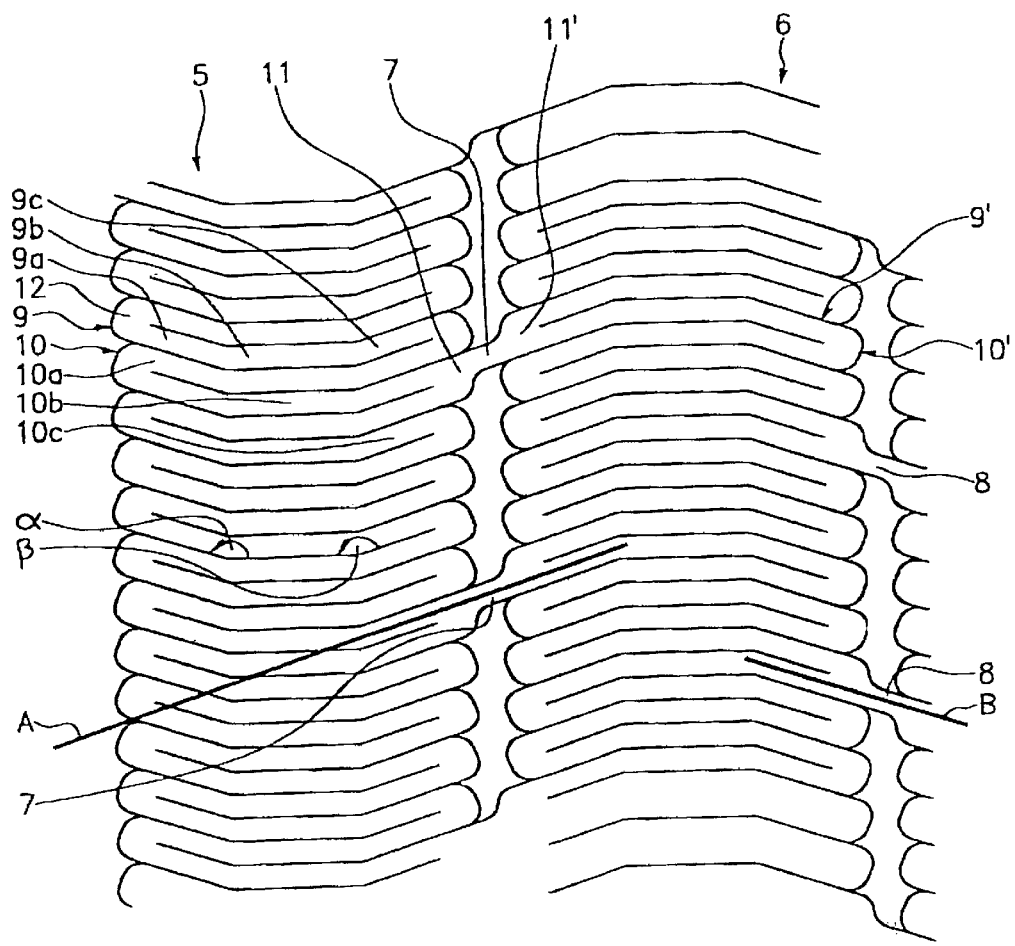
FIG. 4 is an enlarged view showing part of the web structure of the stent in the state according to FIG. 2.

FIG. 4 is an enlarged view showing a section of the web structure 4 in the state according to FIG. 2.

FIG. 4 illustrates that each of the webs 9, 10 comprises three sections 9a to 9c and 10a to 10c, respectively. The sections 9a to 9c have each a straight configuration and adjoin one another to form the previously mentioned plate- or bowl-like configuration. The portions 9a and 9b enclose an obtuse angle α. The central portion 9b and the right portion 9c enclose an obtuse angle β.

Sections 10a and 10c of the web 10 adjoining web 9, which in the illustration chosen in FIG. 4 is positioned below the web 9, are designed accordingly. FIG. 4 illustrates that the webs 9 and 10 which adjoin each other in alternate fashion are each arranged like plates stacked into one another in the non-expanded state of the stent 1. FIG. 4 shows that the previously described configuration of the sections of the webs applies, of course, to each of the webs which jointly form the tubular condition of the wall of the stent 1, as illustrated in FIG. 1, together with the web structure as has been described.

Among each other, webs 9, 10 are interconnected via rounded connection sections 12, of which one connection section 12 is representatively shown in FIG. 4.

A corresponding design applies to webs 9', 10' of the neighboring web pattern 6.

Furthermore, FIG. 4 once again shows the arrangement of the connection elements 7, 8. In the illustration chosen in FIG. 4, the connection elements 7 between the web pattern 5 and the neighboring web pattern 6 have an orientation A which is always the same, i.e. in all connection elements 7. The orientation A is symbolized by a straight line in FIG. 4 and according to FIG. 4 extends from the left side, bottom, to the right side, top.

The orientation of the connection elements 8 is illustrated by line B and extends from the left side, top, to the right side, bottom. The orientation of all connection elements 8 among one another is always the same. Hence, an alternating orientation A, B, A, B, etc. is obtained over the entire web structure.

The connection elements 7, 8 are each configured as straight webs which pass in a straight line into a connection section 11 of the web pattern 5 and into a connection 11' of the web pattern 6, which is symbolically illustrated in FIG. 4 by way of a connection element 7 with its neighboring connection sections 11 and 11', respectively, for all other connection elements 7 and also for 8.

As a result of the design of the webs consisting of three sections and the angles α, β which are arranged between said sections and are preferably obtuse, one achieves, in the spread state illustrated in FIG. 3, an increase in said angles α, β which in a particularly advantageous manner yields the force receiving capacity of the stent in the expanded position. In the non-expanded position the stent is very flexible so that when being passed through body vessels it can very well adapt to curvatures, whereby the implantation process is facilitated considerably.

Figure 5:
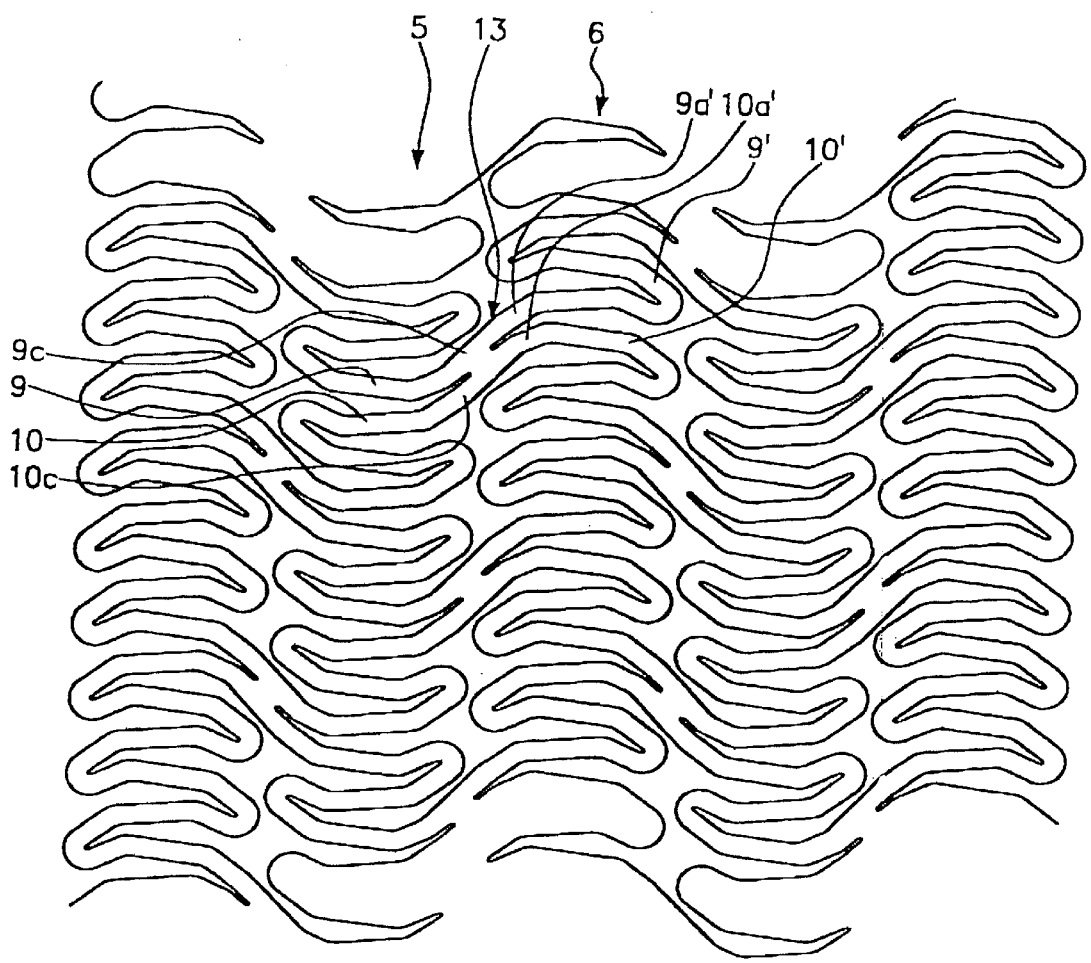
FIG. 5 is a view corresponding to FIG. 3, which shows a second embodiment of the stent according to the invention.

FIG. 5 shows a second embodiment of a stent of the invention according to the illustration of FIG. 3, i.e. in the expanded state.

The basic structure of said embodiment corresponds to that of the previously explained embodiment. Hence, said embodiment also regards a stent having a tubular flexible body whose wall has a web structure which can pass from a non-expanded state into an expanded state as shown in FIG. 5.

The web structure also comprises a plurality of neighboring web patterns, of which two are marked in an exemplary manner in FIG. 5 with reference numerals 5 and 6. The web patterns are again provided with adjoining webs 9, 10 and 9', and 10', respectively. Each of the webs 9, 10 and 9', 10', respectively, is also subdivided into three sections, so that reference can in this respect be made to the above explanation, in particular to FIG. 4.

The embodiment according to FIG. 5 differs from the previously explained embodiment by the absence of any connection elements between the web patterns. FIG. 5 illustrates that in this embodiment the web patterns pass into each other on predeterminable transition sections 13, with neighboring sections of corresponding webs, here: sections 9c and 9'a and 10c and 10'a, respectively, being extended, whereby an integral transition section 13 is formed in each case. As shown in FIG. 5, an symmetrical design of the web patterns is thereby obtained in the area of the transition sections 13, said transition sections 13 having a dimension D greater than the sum of the web widths B1 and B2 for enhancing stiffness.

As becomes apparent from FIG. 5, every third neighboring pair of webs 9, 9' and 10, 10' respectively, has said integral transition section 13 per neighboring web pattern. In principle, however, it is also possible to provide a greater or smaller number of such transition sections 13.

The special advantage of said embodiment is a very compact construction with an equally high flexibility and strength in the expanded state.

Furthermore, FIG. 5 illustrates that the transition sections 13, similar to the connection elements 7, have an alternating orientation; reference can here again be made to the embodiment shown in FIG. 4. Furthermore, FIG. 5 illustrates that, in particular in the expanded state, an H-like configuration of the transition section 13 with the adjoining web sections is obtained.

What is claimed is:

1. A stent (1) comprising a tubular flexible body (2) whose wall (3) has a web structure (4) which can pass from a non-expanded state into an expanded state, wherein the web structure (4) comprises a plurality of neighboring web patterns (5, 6), each web pattern comprising adjoining webs, characterized in that each web comprises three sections arranged relative to one another in a bowl-like configuration.

2. The stent according to claim 1, characterized in that each one of the three sections is straight.

3. The stent according to claim 1, characterized in that a central section of each web intersects adjoining end sections at an obtuse angle ($\alpha$, $\beta$).

4. The stent according to claim 1, characterized in that the web patterns (5, 6) are interconnected by connection elements.

5. The stent according to claim 4, characterized in that the connection elements (7, 8) pass in a straight line into neighboring connection sections (11, 11') of the web patterns (5, 6).

6. The stent according to claim 4, characterized in that all connection elements (7, 8) between directly neighboring web patterns have a common orientation (A, B).

7. The stent according to claim 1, characterized in that neighboring web patterns are joined by transition sections (13).

8. The stent according to claim 7, characterized in that said transition sections (13) are formed by extensions of neighboring sections of adjoining webs.

9. The stent according to claim 1, characterized in that the wall (3) comprises a nickel-titanium alloy.

10. The stent according to claim 1, characterized in that the wall (3) is bio-compatible.

11. A stent comprising a flexible tubular body having a web structure, the web structure having a contracted state for intraluminal delivery and an expanded state for supporting a luminal wall, wherein the web structure comprises a plurality of web patterns formed by adjoining webs, each web comprising three interconnected sections that form a bowl-like configuration.

12. The stent of claim 11 wherein each one of the three interconnected sections is straight.

13. The stent of claim 11 wherein a central one of the three interconnected sections of each web intersects adjoining end sections at an obtuse angle ($\alpha$, $\beta$).

14. The stent of claim 11 wherein the web patterns are interconnected by connection elements.

15. The stent of claim 14 wherein the connection elements join neighboring connection sections along a straight line.

16. The stent of claim 14 wherein all connection elements between directly neighboring web patterns have a common orientation (A, B).

17. The stent of claim 14 wherein the web patterns are interconnected by transition sections formed by extensions of neighboring sections of adjoining webs.

18. The stent of claim 11 wherein the flexible tubular body comprises a bio-compatible nickel-titanium alloy.

\* \* \* \* \*